United States Patent

Jakobi et al.

[11] Patent Number: 5,761,977
[45] Date of Patent: Jun. 9, 1998

[54] CRYOSTATIC MICROTOME

[75] Inventors: Wolfgang Jakobi, Berlin; Christian Niesporek, Wiesloch-Baiertal; Hans Heid, Bammental, all of Germany

[73] Assignee: Carl-Zeiss-Stiftung, Heidenheim, Germany

[21] Appl. No.: 692,647

[22] Filed: Aug. 1, 1996

[30] Foreign Application Priority Data

Aug. 1, 1995 [DE] Germany ............. 195 28 180.2

[51] Int. Cl.$^6$ ............................................. B26D 7/06
[52] U.S. Cl. ............................ 83/13; 83/42; 83/367; 83/370; 83/915.5
[58] Field of Search ..................... 83/13, 42, 364, 83/367, 370, 412, 414, 707, 713, 717, 915.5; 200/47; 355/276

[56] References Cited

U.S. PATENT DOCUMENTS

| | | | |
|---|---|---|---|
| 3,667,330 | 6/1972 | Kobernick | 83/98 |
| 4,484,503 | 11/1984 | Sitte et al. | 83/717 |
| 4,967,629 | 11/1990 | Behne | 83/714 |
| 5,226,335 | 7/1993 | Sitte et al. | 83/915.5 |
| 5,282,404 | 2/1994 | Leighton et al. | 83/13 |
| 5,461,953 | 10/1995 | McCormick | 83/915.5 |

FOREIGN PATENT DOCUMENTS

3500596  7/1986  Germany.

*Primary Examiner*—Maurina T. Rachuba

[57] ABSTRACT

A cryostatic microtome with an automatic approach of the preparation automatically stops the feed movement between the microtome knife and a frozen preparation towards each other upon a mechanical contact between the knife and the preparation. An electrical voltage of a few volts is applied between the microtome knife and the preparation. A small current which appears, due to the intrinsic conductivity of the preparation, upon mechanical contact between the preparation and the microtome knife, and a smaller voltage drop at the preparation resulting therefrom, is current amplified by means of a preamplifier connected as an impedance converter and subsequently measured. The feed movement between the preparation and the microtome knife is automatically stopped when the voltage at the amplifier output falls below a predefined threshold voltage. The preset threshold voltage is temperature dependent and is calculated by a control processor corresponding to the temperature of the cryostat, based on a function and function coefficients. The temperature dependence of the threshold voltage ensures a reliable and precise approach of the preparation throughout the entire temperature range usual in cryomicrotomy.

20 Claims, 4 Drawing Sheets

CRYOSTATIC MICROTOME

BACKGROUND OF THE INVENTION

1. Field of the Invention

This invention relates to a cryostatic microtome with an automatic approach between a frozen preparation and a microtome knife, which automatically stops the feed movement between the microtome knife and the frozen preparation towards each other upon mechanical contact between the two.

2. Discussion of Prior Art

Before starting to cut a preparation to be sectioned with a microtome, or before first starting to cut after a change of the angle between the preparation and the microtome knife, the preparation and the knife first have to be brought into position relative to each other for starting cutting. In principle, the feed mechanism of the microtome can be used for this purpose when, starting from a relatively great distance between the preparation and the knife, the cutting motion is repeatedly carried out, with a succeeding feed between the preparation and the knife, until the first section is taken from the preparation. Since this procedure is however too time-consuming for routine use, in practice the operator sets a rapid feed between the preparation and the microtome knife. However, the precision of this setting, and the time required for it, depend on the experience and skill of the operator.

In order to automate the setting of the starting cut, it has been proposed in U.S. Pat. No. 3,667,330 to provide a limit switch in a motor-driven feed mechanism, so that the rapid feed between the preparation and the microtome knife is automatically stopped when the limit switch is reached. However, it is disadvantageous here that the distance remaining between the preparation and the microtome knife depends on the dimension of the preparation in the direction towards the microtome knife; a relatively large distance remains in the case of preparations with small dimensions, while in the case of preparations which have very large dimensions, the knife already projects relatively far into the preparation, and the preparation can be damaged when the next section is cut.

To solve this problem, it is known from the European Patent Application EP-A1-0544181 of the inventor's assignee to provide a limit switch which is actuated with a release flag by contact of the preparation surface on the knife side. The feed motion is stopped by this arrangement before the preparation surface which faces the knife reaches the plane of the knife. The residual path which remains is in fact constant for each angular setting and can therefore be programmed as the additional travel path. However, after a change of the knife angle, a changed residual path has to be programmed, or a changeover has to be made to another residual path. If the latter is omitted by the user, the approach to the preparation does not work reliably.

In German Laid-Open Patent DE-A1-35 00 596, a microtome is described in which a capacitative distance sensor, formed by the preparation and the microtome knife, is provided to control the section thickness. Such an arrangement is however unsuitable for stopping the feed before cutting is first started—that is, for finding the position at which cutting starts—or before first starting to cut after a change of the angle between the microtome knife and the preparation, since different capacitances are given by the different angles between the preparation surface and the microtome knife, or by different surface shapes with the same distance between the preparation surface and the microtome knife.

It has already been proposed in U.S. Pat. No. 5,282,404, for referencing the relative position of the preparation surface and the microtome knife, to bring the knife and the preparation close enough together for an electrical conductivity to be detectable between the knife and the preparation. This microtome however requires preparations which have an electrically conductive coating. Apart from requiring an additional preparation step, the coating can lead to unforeseen changes or damage to the preparation.

SUMMARY OF THE INVENTION

The invention has as its object to provide a cryostatic microtome which automatically and reliably finds the position for starting cutting, independently of the size and shape of the preparation, in biological preparations which have been prepared in the usual manner for cryostatic microtomy.

This object is attained by means of a cryostatic microtome having:

A microtome knife, a control circuit that automatically stops feed movement of the microtome knife, and a frozen preparation towards each other on mechanical contact between the microtome knife and the preparation, in which an electrical voltage is applied between the microtome knife and the frozen preparation. An electronic circuit detects a change in voltage drop at the frozen preparation or current through the frozen preparation that occurs upon mechanical contact between the microtome knife and the frozen preparation due to the intrinsic conductivity of the frozen preparation, to stop the feed movement.

In the microtome according to the invention, an electrical voltage is applied between the microtome knife and the preparation, and an electronic circuit is provided which detects the appearance of an altered voltage drop at the preparation or a current through the preparation, appearing upon mechanical contact between the microtome knife and the preparation, due to the intrinsic conductivity of the frozen preparation. The feed motion of the microtome knife and preparation towards each other is automatically stopped by a control circuit when a predetermined value of the voltage drop is detected.

The present invention uses the fact that frozen biological preparations which are prepared by standard preparation technology in cryostatic microtomy, i.e., prepared by a simple freezing process without additional measures, have a large content of water of at least 80% of volume and accordingly have a relatively high intrinsic conductivity which depends on the pressure exerted by the knife edge on the preparation, and that a change of the voltage drop at the preparation, caused by the change of the intrinsic conductivity, can be detected with sufficient accuracy. Accordingly, the microtome according to the invention works with uncoated preparations due to the fact that the sensitivity of the electronic circuit is sufficiently high if the resistance of the preparation is more than 1 megaohm and varies, depending on temperature, between 5 and 200 megaohm.

It has been found to be particularly suitable to provide a control circuit which stops the feed motion, in dependence on the respective temperature of the preparation, at different values of the voltage drop at the preparation or current through the preparation. The temperature dependence of the change of conductivity of the preparation can thereby be compensated over a region which is wide enough to set the position of starting cutting with high accuracy for all usual cutting temperatures in the range of −10° C. through −50° C. A temperature sensor is provided, in the vicinity of the preparation in the cryostat, for the determination of the preparation temperature.

The electrical voltage applied between the microtome knife and the preparation should preferably be between three and sixty volts. This is because at low voltages the voltage drop is not detectable with sufficient accuracy at all usual temperatures due to the strong temperature dependence of the conductivity of the preparation, and because technical safety problems arise at voltages of higher than 60 volts. In addition, changes in the preparation due to the electrical voltage or to the electrical current through the preparation are to be expected.

The applied electric voltage is preferably the same as the supply voltage of a measurement preamplifier of the electronic circuit. No additional change of voltages is necessary. The measurement preamplifier can be connected as an impedance converter, and thus with an amplifier output coupled back to the inverting input. The non-inverting input of the measurement preamplifier is to be conductively connected to the preparation, or to the knife of the microtome, and via a high-ohmic resistor to the voltage supply of the measurement preamplifier. The high-ohmic resistor and the preparation then form a voltage divider circuit, and the voltage drop over the preparation corresponds to the difference of the supply voltage and the voltage drop over the high-ohmic resistor. The value of the high-ohmic resistor should be at least 10 megohms, preferably at least 22 megohms, so that a sufficient change of the voltage drop at the preparation is detectable even at preparation temperatures between −30° C. and −50° C.

In order to apply an electrical voltage between the microtome knife and the preparation, both parts have to be insulated relative to each other. For this purpose the object holder which serves to receive a preparation table is advantageously received on an electrically insulating insulator on the microtome. The electrical insulation is then situated at a place where contamination with residues of cutting, which can possibly cause an electrical short circuit between the preparation and the microtome knife, is completely excluded. The insulator should comprise a ceramic or a glass-reinforced plastic, in order to prevent any appreciable deformation of the insulator by the cutting forces which arise.

The measurement preamplifier should be arranged as close as possible to the preparation, so that the stray electromagnetic radiation caused by the microtome motor does not interfere with the measurement of the voltage drop. It is particularly advantageous to make the insulator a hollow cylinder for this purpose, and to arrange the measurement preamplifier, including the high-ohmic resistor and electronic low pass filters, within the hollow cylindrical insulator.

BRIEF DESCRIPTION OF THE DRAWINGS

Details of the invention are described in more detail below, with reference to a preferred embodiment shown in the accompanying drawings, in which.

DETAILED DESCRIPTION OF THE PREFERRED EMBODIMENTS

Figure 1:
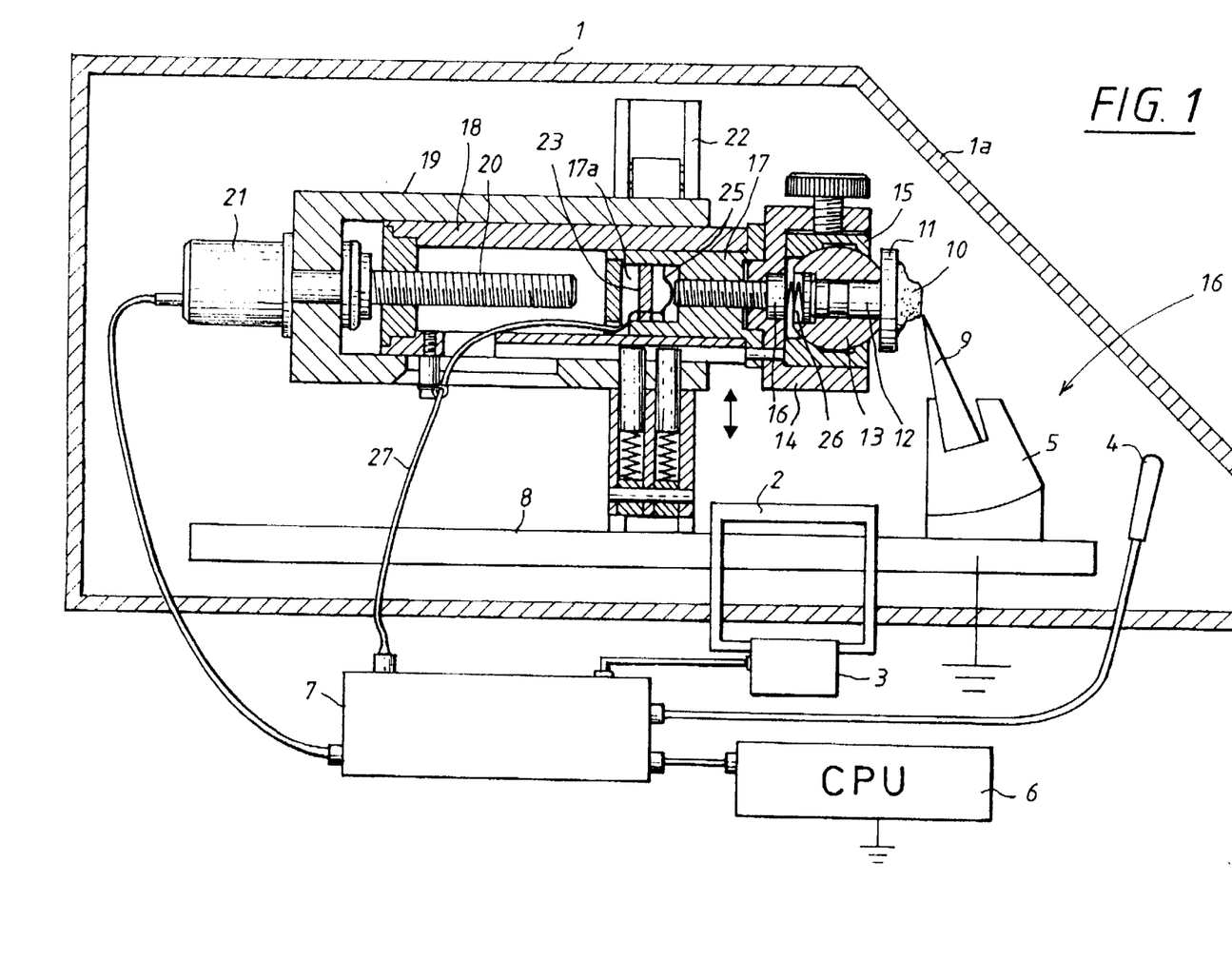
FIG. 1 shows a section through a cryostatic microtome according to the invention, in the region which contains the microtome knife and the preparation carrier.

The cryostatic microtome in FIG. 1 has a thermally insulated cryostat housing, which is known per se, and whose insulating outer wall (1) includes an opening flap (1a). An opening flap (1a) of a transparent material is provided at the front side of the cryostat, so that the microtome in the interior space (1b) of the cryostat housing is accessible for changing the preparation or knife, and for cleaning. The internal space (1b) of the cryostat can be cooled from the ambient temperature down to −50° C. by means of a heat exchanger (2) which is provided in the interior (1b) of the cryostat and which is connected to a compressor outside the cryostat. The usual working temperature of the cryostat then lies in the region from −10° C. to −50° C. The temperature in the internal space (1b) of the cryostat is continuously measured by means of a temperature sensor (4), and the cooling power of the compressor (3) is regulated such that the temperature measured with the temperature sensor (4) corresponds to the desired temperature, which is set by the user on a panel (not shown). For this regulation of the cryostat temperature, the temperature sensor (4), the compressor (3), and a control processor (6) are connected together by means of a connecting unit (7). The connecting unit (7) thus represents the interface between the individual parts of the equipment.

Furthermore, the microtome is arranged in the internal space (1b) of the cryostat. It includes a fixed metallic baseplate (8), which is at ground potential, and on which a metallic knife holder (5) is arranged with a knife (9), likewise of metal, received in it.

The preparation (10) to be sectioned is received on an object table (11). For a rapid and simple change of preparations, the object table (11) has a cylindrical bolt (12) which can be clamped in a joint ball (13). To change the preparation (10), the object table (11) can be pulled horizontally forwards after the release of a clamping screw (not shown) from the joint ball (13), and can be exchanged for another object table with another preparation.

The joint ball (13) serves for setting the relative orientation between the preparation (10) and the microtome knife (9). The joint ball (13) is rotatably received for this purpose in a cylinder head (14), and the position of the joint ball (13) which has been set can be clamped by means of clamp jaws (15).

The cylinder head (14) is screwed to a cylindrical insulator (17) by means of an electrically conducting screw (16). The insulator (17) consists of a high strength, electrically insulating material, for example a ceramic or a glass fiber reinforced plastic.

The insulator (17) is furthermore mainly received within a metallic hollow cylinder (18), and this hollow cylinder (18) is received, horizontally movable, in a metallic cylinder guide (19). The metallic hollow cylinder (18) is displaced horizontally relative to the cylinder guide (19) for the feed motion between the preparation (10) and the microtome knife (9), that is, in order to bring the preparation (10), before it is sectioned, into the vicinity of the microtome knife (9), and after this to feed the preparation forward by the predetermined section thickness after each cut. A stepping motor (21), with a threaded rod (20), is provided on the cylinder guide (19), and an internal thread, matching the threaded rod (20), is provided on the hollow cylinder (18).

The hollow cylinder (18), its internal thread, the cylinder guide (19) and the threaded rod (20) of the stepping motor (21) are all coaxially arranged for this purpose.

In order to carry out the cutting motion, the cylinder guide (19) is received, movable perpendicularly with respect to its cylinder axis, on a guide path 22, which is itself fixedly connected to the baseplate (8) of the microtome. In order to carry out microtome sectioning, the cylinder guide (19) is moved in the vertical direction, as indicated by the double arrow.

Figure 2:
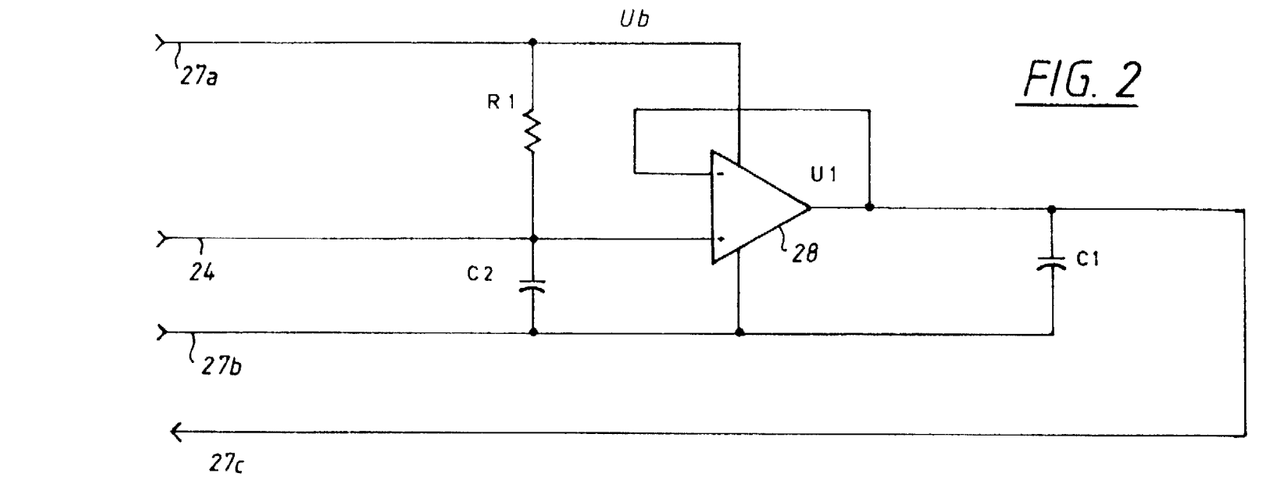
FIG. 2 shows a circuit diagram of the measurement amplifier integrated into the preparation carrier.

The insulator (17) has a recess (17a)in a region which extends into the interior of the hollow cylinder (18), and is thus partially formed as a hollow cylinder. A board (23) with the preamplifier circuit, which is shown in FIG. 2 and is described below in more detail, is arranged in this recess (17a). The input of the preamplifier circuit is connected to a resilient metal plate (25) which is likewise arranged in the recess (17a)of the insulator (17), and on which the screw (16) for fastening the cylinder head (14) presses. Furthermore, a metallic compression spring (26) is provided between the head of the screw (16) and the bolt (12) of the object table (11). The metallic object table (11) is in this manner connected for electrical conduction to the input of the preamplifier board (23), so that simple and rapid interchangeability of the object table (11) and cylinder head (14) is ensured by the metallic springs (25, 26). At the same time, as short as possible a conductive connection between the preparation (10) and the preamplifier board (23) is ensured by the arrangement of the preamplifier board (23) in the recess (17a)of the insulator (17). This measure prevents the interjection of stray electrical signals, for example from the stepping motor (21) or from the drive motor (not shown) for the vertical movement of the cylinder guide (19), particularly into the input of the preamplifier.

The output of the preamplifier board (23) and the voltage supply of the preamplifier take place through a three-conductor cable (27) which is passed out through openings in the hollow cylinder (18) and in the cylinder guide (19) and is connected to the connecting unit (7). The output signals from the preamplifier are passed to the control processor (6). The required analog/digital converter for the measured signals and also the low voltage supply unit for the preamplifier board (23) are provided on the control processor (6) board.

The circuit arranged on the preamplifier board (23) is shown in detail in FIG. 2. It essentially consists of a measuring amplifier (28), the output of which is coupled back to the inverting input, thus representing an impedance converter. The supply leads of the operational amplifier (28) are denoted by (27a) and (27b), the lead (27a) being connected to the positive supply voltage of 5 volts, and the lead (27b) being connected to the ground potential. A first capacitor (C1), with a capacitance of 10 μF, is connected between the output (27c)of the operational amplifier (28) and the ground lead (27b), and forms with the output resistance of the measuring amplifier (28) a low pass filter with a cutoff frequency of about 100 Hz. Interfering signals which are interjected into the output lead (27c)between the operational amplifier (28) and the connecting unit (7) are damped by this low pass filter. A second capacitor (C2) with a capacitance of 0.33 nF, is connected between the ground lead (27b)and the non-inverting input of the measuring amplifier (28), and a resistor (R1) of 22 megohms is connected between the positive supply lead (27a)of the measuring amplifier (28) and the non-inverting input. The second capacitor (C2) forms, with the resistor R1, a low pass filter with a cutoff frequency of 25 Hz. Interference which is interjected between the preparation (10) and the non-inverting input of the measuring amplifier (28) is damped by this low pass filter.

The non-inverting input of the measuring amplifier (28) represents the input of the preamplifier circuit and is conductively connected to the metal plate (24), and thus to the preparation (10). As long as the preparation (10) and the knife (9) are spaced apart from each other, and consequently no electrically conducting connection exists between the preparation (10) and the microtome knife (9), which is at ground potential, the preparation (10) is connected via the resistor R1 to the supply voltage $U_b$, of +5 V, of the measuring amplifier (28). A voltage of 5 V is thus present between the preparation (10) and the microtome knife (9). In the case of a mechanical contact between the microtome knife (9) and the preparation (10), the intrinsic conductivity of the preparation (10) is increased by the pressure exerted by the microtome knife (9) on the frozen preparation (10). The cause of this is presumably that ice crystals within the preparation (10) are melted by the pressure exerted by the sharp knife blade and hence increase the conductivity. The electrical resistance of the preparation is then dependent on both the specimen thickness and on the cryostat temperature. According to the specimen thickness, it amounts to about 7–10 megohms at −10° C. and to about 200 megohms at −50° C. This resistance of the preparation and the resistance (R1) of the preamplifier circuit form a voltage divider circuit. The voltage applied to the non-inverting input of the measuring amplifier (28) is therefore lower, the higher the intrinsic conductivity of the preparation (10). This drop of the voltage at the non-inverting input of the measuring amplifier (28) produces at the amplifier output (27c) a nearly identical current amplified voltage change, which is detected by the control processor (6) on reaching a predefined threshold voltage ($U_s$). The stepping motor (21), and thus the feed of the preparation, is then stopped by the control processor (6).

Since the intrinsic conductivity of the preparation is strongly temperature-dependent, the feed movement is stopped at different threshold voltages ($U_s$) at the output of the preamplifier, in dependence on the temperature measured with the temperature sensor (4).

Figure 3:
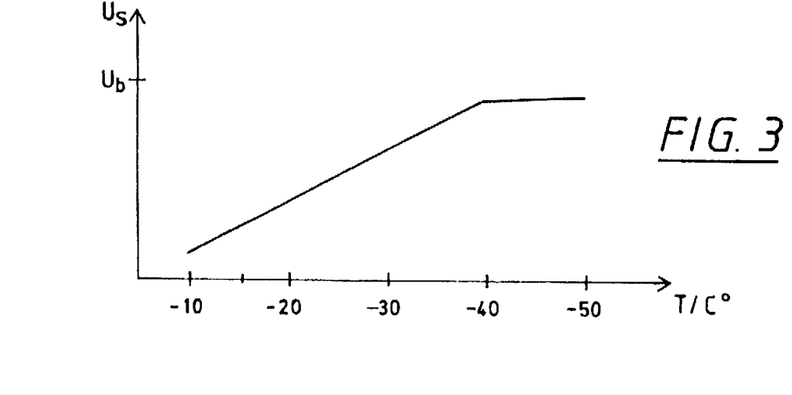
FIG. 3 shows a diagram of the voltage drop to stop the feed movement, as a function of the cryostat temperature.

This temperature dependence of the threshold voltage ($U_s$) is shown in FIG. 3. At a resistance (R1) of 22 megohms, it runs linearly between −10° C. and −40° C., and has at −10° C. a value of 12.5%, and at −40° C. a value of 94%, of the output voltage of the amplifier appearing in the absence of contact between the preparation and the microtome knife, and substantially corresponding to the supply voltage ($U_b$). At temperatures below −40° C., the threshold voltage ($U_s$) remains constant at 94% of this output voltage. At temperatures between −10° C. and −40° C., the dependence of the threshold voltage on the temperature is calculated by the control processor (6) according to the formula $U_s=a*(T-T_o)+b$, based on the actual value of the temperature. Here T is the value of the temperature, and $T_o$ is the maximum permissible temperature of −10° C.; the factor a amounts to 0.12 V/° C. The coefficient b corresponds to ⅛ of the output voltage of the amplifier in the absence of contact between the preparation and the microtome knife. The value of the threshold voltage ($U_s$) at any given time is used by the processor, according to the cryostat temperature, for the detection of the contact between the preparation and the microtome knife, the value of the threshold voltage for −40° C. being used at temperatures between −40° C. and −50° C.

Figure 4:
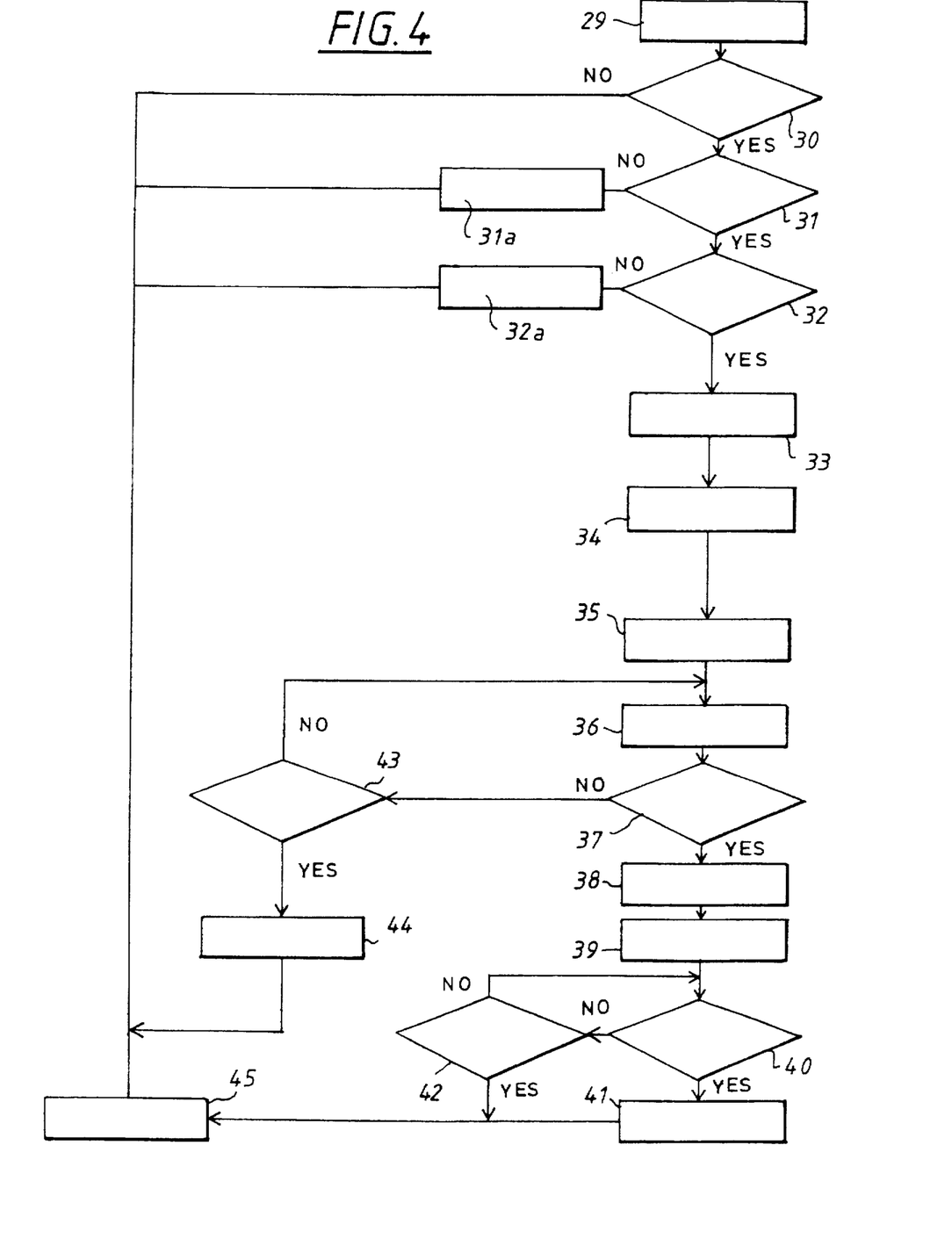
FIG. 4 shows a flow diagram of the feed control circuit during sectioning of a specimen.

The function steps which proceed automatically in the microtome according to the invention are shown as a block diagram in FIG. 4. If the operator actuates a key (29) on the input panel (not shown) for the automatic approach of the preparation, after a new or other preparation has been inserted, in a step (30) the control processor (6) first interrogates whether the object table is located at the height of the microtome knife. If this is not the case, in a microtome with a manual drive of the cutting movement, the routine is left by reaching step (45). In a microtome with motor drive of the cutting movement, the object table is automatically set to the height of the microtome knife.

After the object table has reached the height of the microtome knife, it is tested in step (31) whether the cryostat temperature measured with the temperature sensor (4) is in the permissible region between −10° C. and −50° C. If this is not the case, an error message is produced in step (31a) and is displayed on a display (not shown). If the temperature is in the permissible region, it is tested in a succeeding step (32) whether the output voltage of the preamplifier is at least 96% of the supply voltage ($U_b$). If this condition is not fulfilled, an error message is generated in a step (32a), indicating to the user that a contact between the preparation and the microtome knife already exists. If the output voltage of the preamplifier is higher than 96% of the supply voltage, in step (33) the present output voltage is measured, and in step (34) the threshold voltage ($U_s$) is calculated according to the above equation, based on the present output voltage and the present temperature value. Thereafter, in step (35), the stepping motor (21) for specimen feed is started and the preparation is moved towards the microtome knife (horizontal movement). During the movement of the preparation, the output voltage of the preamplifier is constantly measured in step (36), and it is tested in step (37) whether the output voltage is already smaller than the calculated threshold voltage ($U_s$). If the threshold voltage is smaller than the output voltage, it is tested in an interrogation (43) whether the user, by the actuation of a corresponding key, has given an order to abort the automatic approach of the preparation. If this is the case, the stepping motor (21) is stopped in step (44), and the routine is left in function step (45); otherwise, the movement of the stepping motor (21) is continued, until the output voltage of the preamplifier (28) is smaller than the threshold voltage ($U_s$), and the stepping motor is stopped by reaching function step (38). Thereafter, in step 39, the stepping motor (21) is reversed and the preparation is moved away from the microtome knife by 200 μm. In a succeeding interrogation loop (40), it is tested whether the object table is located in the highest position. If this is not the case, it is tested in step (42) whether the user has given an abort order. If this is also not the case, the interrogations (40, 42) are asked again, until one of the interrogations is answered Yes. Light beams are provided in a conventional manner for the detection of the uppermost position of the object table.

If the object table is in the uppermost position at the time of an interrogation (40), in a closing step (41) the movement of the stepping motor (21) is again reversed and the preparation is moved towards the microtome knife by the same amount—that is, by 200 μm—as in step (39), and after this the routine is left by reaching the function step (45). The sectioning of the preparation can thereafter be begun, and the preparation can be sectioned in the usual manner.

By the separation of the preparation and the knife in step (39), it is ensured that when the object table is caused to travel back to its uppermost position, the preparation and the knife are mutually spaced apart, and no damage to the preparation can occur. The return travel of the object table into its uppermost position can take place automatically in a microtome which has motorized drive of the cutting movement.

In a microtome which has motorized drive for the cutting movement the invention can be used in addition to detect an automatic cutting window. Microtomes with motorized cutting movement run at controlled speed. The speed control represents a closed feedback loop in which a setpoint of speed is adjustable usually by a potentiometer and where an actual speed value is detected from the movement. This detection is usually arranged by a tacho-generator on the drive motor or by incremental encoders at any location of the drive movement. The speed itself is selected for best sectioning results for the specimen to be cut. This may vary with the desired thickness of the section to be cut and with the consistency of the specimen tissue.

After a cut with a vertical stroke a return stroke takes place back to the upmost position. In order to reduce the time consumed for this return stroke it is common practice to carry out this part of the complete motorized movement with a higher speed.

Advanced instruments feature an adjustable cutting window (zone). This cutting window can be predetermined prior to cutting via keyboard control and the reading of a position sensor. It is useful to select a cutting window slightly larger than the vertical dimension of the specimen to be cut. As a result, the selected cutting speed of the motorized cutting movement is carried out only when passing the cutting window while the movement outside that cutting window is carried out with a higher speed. This procedure shortens the cutting process but allows cutting the specimen at the selected lower speed.

The invention also can be used to provide a cryostatic microtome with motorized cutting movement that automatically determines an optimized cutting window independently of the size and shape of a biological preparation. This is attained by means of the same microtome with the same detecting measures used for the automatic detection to find the position to begin cutting described for the present invention. The present invention has a motorized cutting movement with a position sensor for the cutting movement and has additional software that uses the detected signals of the preamplifier to determine the optimized cutting window for the motorized cutting movement.

After the contact of the preparation with the knife edge and the subsequent reverse movement of the preparation of 200 μm in the horizontal direction as described above, the motorized cutting drive can be started from the keyboard. The preparation moves upwards with high return travel speed until the upmost position is detected by the position sensor for the cutting movement. In this position, the horizontal feed drive is delivering the retracted amount of 200 μm plus an amount of a preselected cutting thickness. Then the first portion of the downstroke takes place with the preselected cutting speed. During this downstroke movement a signal is transferred to the processor from the preamplifier when the knife edge is touching the specimen and the signal continues until the section is completed. When the signal occurs the reading of the position sensor is stored in the memory of the processor. When the signal changes its value again because the preparation is completely cut and the knife no longer has contact with the specimen the reading of the position sensor is again stored in the memory. The difference between both stored readings of the position sensor now represents a measure of the vertical size of the preparation. The cutting window to be determined from these measurements should be slightly larger to allow the system to slow down from the faster return travel speed to the slower cutting speed. This determination takes place by adding corrective amounts to the measured distance. This calculation finally determines the cutting window for the next downstroke. During the next downstroke the same measurements and calculations take place again in order to determine the cutting window for the then next following downstroke. As a result an optimized cutting window is always present even for preparations of irregular or conical shape.

Figure 5:
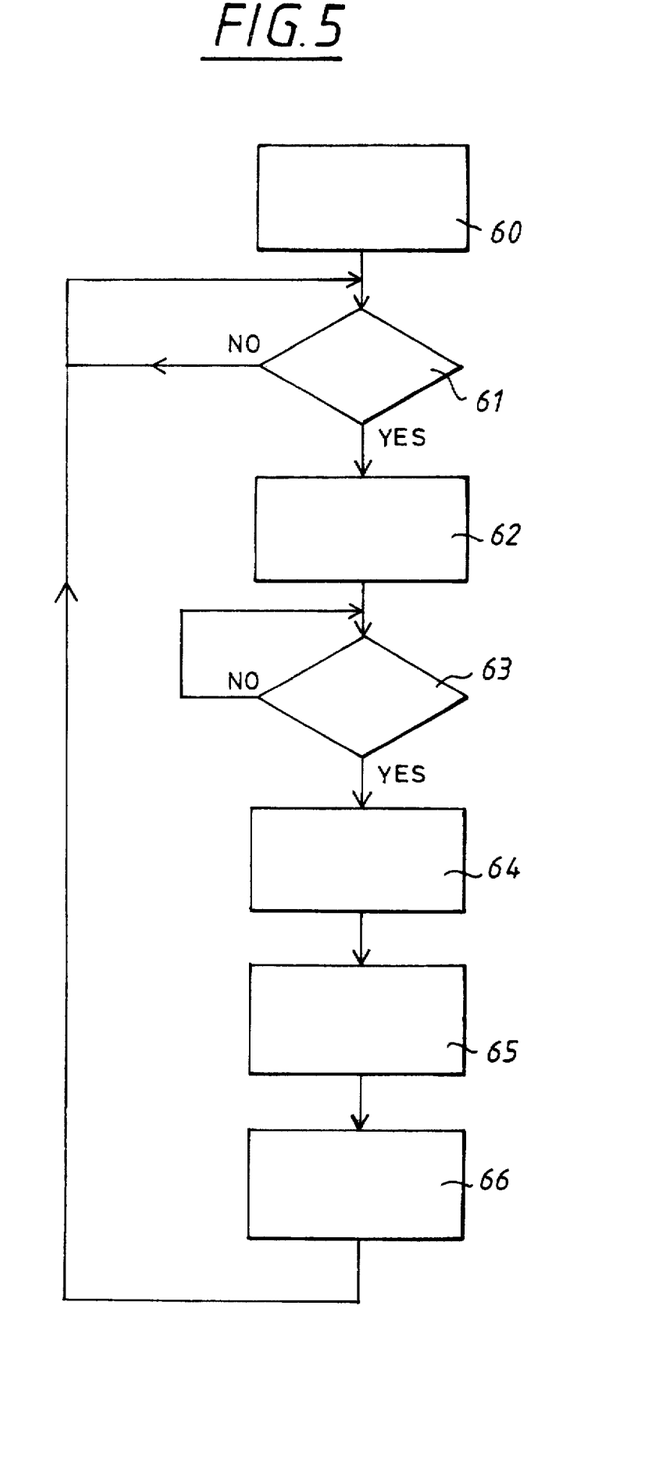
FIG. 5 shows a flow diagram of a circuit for automatic detection and automatic setting of a cutting window.

The function steps which proceed automatically in the microtome to determine an optimized cutting window are shown as a block diagram in FIG. 5. If the operator actuates a key to start the motorized cutting movement of the microtome, after an automatic approach between the knife edge and a preparation takes place, the return travel to the upmost position is carried out and the horizontal feed drive delivers the retracted amount of 200 µm plus the selected cutting thickness. Then the downstroke starts with the preselected cutting speed in a step (60). Then the control processor (6) first tests in step (61) whether a signal change from the preamplifier is detected. If not, the process continues as before via step (60). If there is a signal change because the preparation has reached the knife edge, the actual reading of the position sensor is taken and stored in the memory of the processor in step (62) and the movement continues with the preselected cutting speed. In step (63) the processor tests whether the signal changes back because the preparation is leaving the contact with the knife. If not, the process continues as before. If yes, the actual reading of the position sensor is taken and stored in the memory of the processor in step (64). In the next step (65) a calculation takes place in which corrective amounts are added to the measurement distance in order to determine the cutting window for the following stroke. In step (66) the control processor forces the motorized cutting drive to carry out a return stroke and a first part of the downstroke with the higher return speed and then to carry out a slower cutting movement while passing the cutting window calculated in step (65). During the passage the cutting window for the next downstroke is determined as described above. This process continues as long as the motorized cutting drive is actuated leading to a continuously optimized automatic cutting window.

In the embodiments described, the threshold voltage ($U_s$) is always calculated anew, based on the output voltage of the preamplifier when there is no contact between the preparation and the microtome knife. Alternatively, a data table of threshold voltages belonging to the respective temperature could be stored in a memory. Instead of a calculation of the threshold voltages, the value belonging to the present temperature would only have to be selected from the table. However, this would have the disadvantage, as against the described embodiment, that either the preamplifier would have to be selected such that the same output voltage is always present, within narrow limits, in the absence of contact between the knife and the preparation, or that an individual data table would have to be determined for the control circuit of each individual equipment. In contrast to this, the output voltages of the preamplifier can vary within a series by 4–5% in the described embodiment, and the same value, given above, for the function coefficient a can always be used.

In the embodiment shown in the Figures, the preamplifier is arranged on the preparation side. It is of course also possible to insulate the knife holder from the baseplate of the microtome and to arrange the preamplifier board in this insulation in the vicinity of the knife holder, the knife holder then being connected to the amplifier input. With this alternative, the insulation is of course exposed to more severe contamination by cutting residues, due to which a short circuit between the knife and the preparation, and hence a premature stopping of the feed movement, can result.

We claim:

1. A cryostatic microtome for sectioning frozen preparations comprising:
    a microtome knife,
    a control circuit that automatically stops feed movement of said microtome knife and a frozen preparation towards each other on mechanical contact between said microtome knife and said frozen preparation wherein an electrical voltage is applied between said microtome knife and said frozen preparation, and
    an electrical circuit that detects a changed voltage drop at said frozen preparation or current through said frozen preparation that occurs upon mechanical contact between said microtome knife and said frozen preparation due to intrinsic conductivity of said frozen preparation to stop said feed movement,
    whereby sensitivity of said electronic circuit is sufficiently high for detecting a changed voltage drop at said frozen preparation or current through said frozen preparation when resistance of said frozen preparation is more than 1 megaohm.

2. The cryostatic microtome according to claim 1, further comprising a temperature sensor, wherein said control circuit is arranged to stop said feed movement at a predetermined value ($U_s$) for said voltage drop at said frozen preparation or said current through said frozen preparation, and wherein said predetermined value ($U_s$) varies in dependence on cryostat temperature.

3. The cryostatic microtome according to claim 1, wherein said electrical voltage is at most sixty volts.

4. The cryostatic microtome according to claim 1, wherein said electronic circuit includes a measuring preamplifier and said electrical voltage corresponds to a supply voltage ($U_b$) of said measuring preamplifier.

5. The cryostatic microtome according to claim 4, wherein said measuring preamplifier is arranged as an impedence converter.

6. The cryostatic microtome according to claim 4, wherein said measuring preamplifier has an input connected for electrical conduction to said frozen preparation or to said microtome knife via a high-ohmic electrical resistor (R1) to a voltage supply of said measuring preamplifier.

7. The cryostatic microtome according to claim 6, wherein said high-ohmic electrical resistor has a resistance of at least 10 megohms.

8. The cryostatic microtome according to claim 6, wherein said high-ohmic electrical resistor has a resistance of about 22 megohms.

9. The cryostatic microtome according to claim 1, further comprising an object table, an object holder for receiving said object table, and an electric insulator for receiving said object holder.

10. The cryostatic microtome according to claim 9, wherein said insulator has a recess and said measuring preamplifier is arranged in said recess of said insulator.

11. The cryostatic microtome according to claim 9, wherein said insulator comprises a ceramic or a glass fiber reinforced plastic.

12. The cryostatic microtome according to claim 1, wherein said control circuit is arranged to automatically reverse movement between said frozen preparation and said microtome knife after stopping said feed movement and to move said frozen preparation and said microtome knife away from each other by a predetermined path length, and to move said microtome knife and said frozen preparation together again by a predetermined path length after reaching an upper most position of said frozen preparation.

13. A cryostatic microtome according to claim 2, wherein said control circuit is programmed to calculate said predetermined value of said voltage drop ($U_s$) based on function coefficients.

14. A process for operation of cryostatic microtome, comprising:
- as a first step, feed moving a microtome knife and a frozen preparation towards each other, in which resistance of said frozen preparation is more than 1 megaohm, and
- as a second step, automatically stopping said feed movement upon mechanical contact between said microtome knife and said frozen preparation by applying an electrical voltage between said frozen preparation and said microtome knife and detecting current through said frozen preparation or voltage drop at said frozen preparation and arising due to intrinsic conductivity of said frozen preparation.

15. A cryostatic microtome for sectioning frozen preparations comprising:
- a microtome knife,
- a control circuit that automatically stops feed movement of said microtome knife and a frozen preparation towards each other on mechanical contact between said microtome knife and said frozen preparation wherein an electrical voltage is applied between said microtome knife and said frozen preparation,
- an electrical circuit that detects a changed voltage drop at said frozen preparation or current through said frozen preparation that occurs upon mechanical contact between said microtome knife and said frozen preparation due to intrinsic conductivity of said frozen preparation to stop said feed movement, and
- a temperature sensor,
- wherein said control circuit is arranged to stop said feed movement at a predetermined value ($U_s$) for said voltage drop at said frozen preparation or said current through said frozen preparation, and wherein said predetermined value ($U_s$) varies in dependence on cryostat temperature.

16. A cryostatic microtome for sectioning frozen preparations comprising:
- a microtome knife,
- a control circuit that automatically stops feed movement of said microtome knife and a frozen preparation towards each other on mechanical contact between said microtome knife and said frozen preparation wherein an electrical voltage is applied between said microtome knife and said frozen preparation, and
- an electrical circuit that detects a changed voltage drop at said frozen preparation or current through said frozen preparation that occurs upon mechanical contact between said microtome knife and said frozen preparation due to intrinsic conductivity of said frozen preparation to stop said feed movement,
- wherein said electrical voltage is at most sixty volts.

17. A cryostatic microtome for sectioning frozen preparations comprising:
- a microtome knife,
- a control circuit that automatically stops feed movement of said microtome knife and a frozen preparation towards each other on mechanical contact, between said microtome knife and said frozen preparation wherein an electrical voltage is applied between said microtome knife and said frozen preparation,
- an electrical circuit that detects a changed voltage drop at said frozen preparation or current through said frozen preparation that occurs upon mechanical contact between said microtome knife and said frozen preparation due to intrinsic conductivity of said frozen preparation to stop said feed movement,
- wherein said electronic circuit includes a measuring preamplifier and said electrical voltage corresponds to a supply voltage ($U_b$) of said measuring preamplifier.

18. A cryostatic microtome for sectioning frozen preparations comprising:
- a microtome knife,
- a control circuit that automatically stops feed movement of said microtome knife and a frozen preparation towards each other on mechanical contact between said microtome knife and said frozen preparation wherein an electrical voltage is applied between said microtome knife and said frozen preparation,
- an electrical circuit that detects a changed voltage drop at said frozen preparation or current through said frozen preparation that occurs upon mechanical contact between said microtome knife and said frozen preparation due to intrinsic conductivity of said frozen preparation to stop said feed movement,
- an object table,
- an object holder for receiving said table, and
- an electric insulator for receiving said object holder,
- wherein said insulator has a recess and said measuring preamplifier is arranged in said recess of said insulator.

19. A cryostatic microtome for sectioning frozen preparations comprising:
- a microtome knife,
- a control circuit that automatically stops feed movement of said microtome knife and a frozen preparation towards each other on mechanical contact between said microtome knife and said frozen preparation wherein an electrical voltage is applied between said microtome knife and said frozen preparation,
- an electrical circuit that detects a changed voltage drop at said frozen preparation or current through said frozen preparation that occurs upon mechanical contact between said microtome knife and said frozen preparation due to intrinsic conductivity of said frozen preparation to stop said feed movement,
- an object table,
- an object holder for receiving said object table, and
- an electric insulator for receiving said object holder,
- wherein said insulator comprises a ceramic or a glass fiber reinforced plastic.

20. A cryostatic microtome with motorized cutting movement for sectioning frozen preparations, said frozen preparations having boundaries in a direction of said cutting movement and said cutting movement having a speed, said microtome comprising:
- a microtome knife,
- an object table for receiving said frozen preparations,
- an electrical isolator by which said knife and said object table are electrically isolated with respect to one another,
- a voltage source by which an electrical voltage is applied between said knife and said object table,
- an electronic circuit that detects a changed voltage drop at said frozen preparations or current through said frozen preparations that occurs upon mechanical contact between said microtome knife and said frozen preparations due to intrinsic conductivity of said frozen preparations, whereby said electronic circuit generates first and second position values representing said boundaries of said frozen preparations in said direction of cutting movement, and a control circuit that automatically adjusts said speed of said cutting movement between said first and second position values within a cutting process to a preselected cutting speed and automatically adjusts said speed of cutting movement to a higher return travel speed while completing said cutting process.

* * * * *